US005322515A

United States Patent [19]

Karas et al.

[11] Patent Number: 5,322,515
[45] Date of Patent: Jun. 21, 1994

[54] LUER ADAPTER ASSEMBLY FOR EMERGENCY SYRINGE

[75] Inventors: Peter J. Karas; Larry W. Pitts, both of Libertyville; John C. Tanner, II, Lake Bluff, all of Ill.

[73] Assignee: Abbott Laboratories, Abbott Park, Ill.

[21] Appl. No.: 31,789

[22] Filed: Mar. 15, 1993

[51] Int. Cl.$^5$ .............................................. A61M 5/32
[52] U.S. Cl. ................................... 604/192; 604/218; 604/232; 604/283; 128/919
[58] Field of Search ............... 604/192, 263, 187, 218, 604/905, 232, 283; 128/919

[56] References Cited

U.S. PATENT DOCUMENTS

| 4,232,669 | 11/1980 | Nitshke | 604/263 X |
| 4,834,716 | 5/1989 | Ogle | 604/192 |
| 5,084,032 | 1/1992 | Kornberg et al. | 604/263 |
| 5,088,985 | 2/1992 | Deras | 604/192 |
| 5,098,400 | 3/1992 | Crouse et al. | 604/192 |
| 5,151,090 | 9/1992 | Best et al. | 604/192 |

FOREIGN PATENT DOCUMENTS

| 3842317 | 6/1990 | Fed. Rep. of Germany | 604/263 |
| 9007913 | 7/1990 | PCT Int'l Appl. | 604/263 |

Primary Examiner—C. Fred Rosenbaum
Assistant Examiner—N. Kent Gring
Attorney, Agent, or Firm—A. Nicholas Trausch

[57] ABSTRACT

A luer adapter assembly for a prefilled emergency syringe includes a cylindrical sheath which extends coaxially with the syringe needle. The sheath can be integrally molded with the injector housing or is attached to the syringe injector housing by spin welding or sonic welding. The sheath is joined to the housing so that an annular clearance space for the removable luer adapter assembly is maintained between the tapered hub and the sheath. A removable cap on a threaded lock on the adapter extension is removed by twisting the cap in a first direction. The whole adapter assembly is removed from the tapered hub by twisting the cap in a second direction which is the same direction as the threads of the threaded lock.

6 Claims, 2 Drawing Sheets

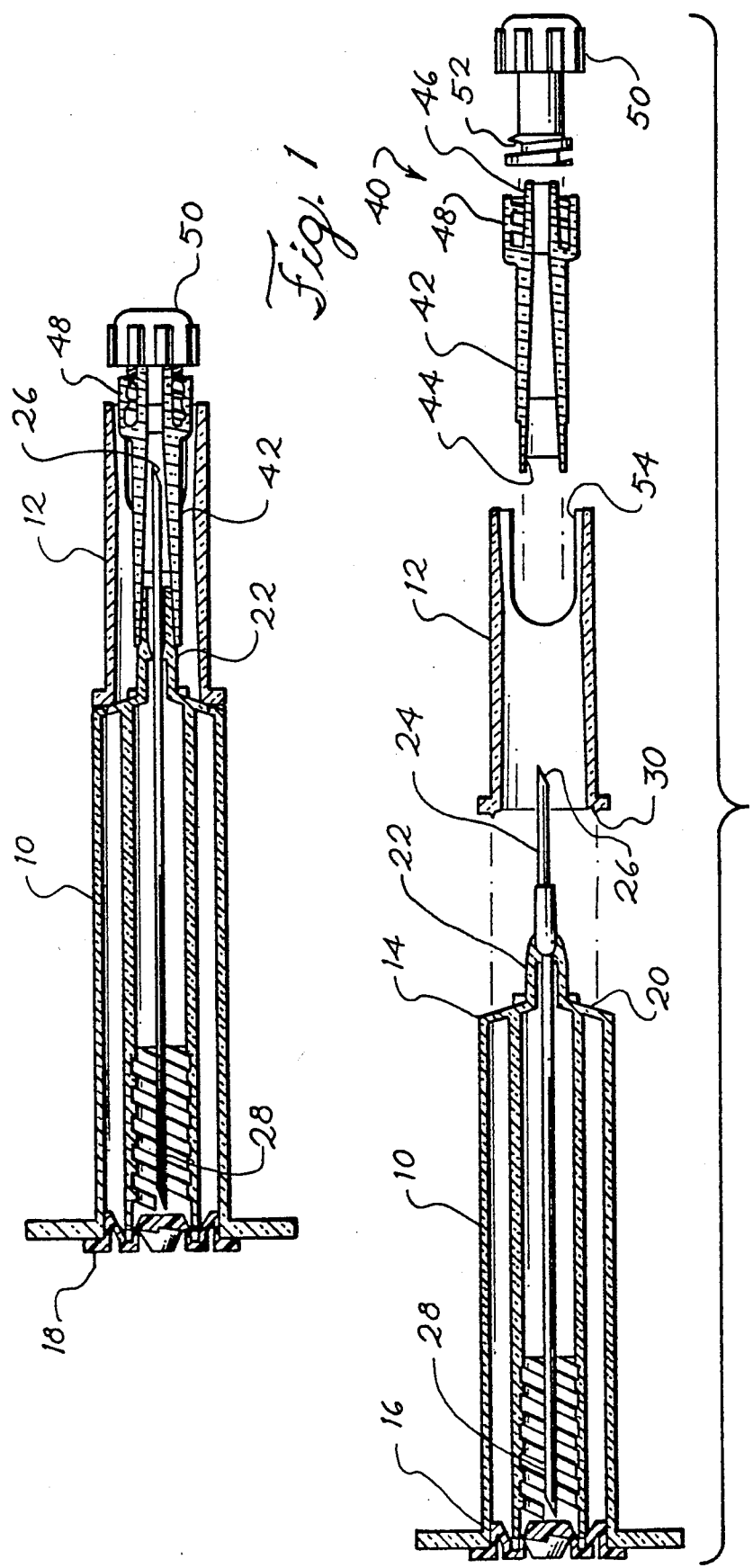

LUER ADAPTER ASSEMBLY FOR EMERGENCY SYRINGE

FIELD OF THE INVENTION

The present invention relates to a prefilled emergency syringe and in particular to a luer adapter assembly for a prefilled emergency syringe of the type having an integral extending cannula and optionally a hollow protective sheath.

BACKGROUND OF THE INVENTION

The Abboject ® prefilled emergency syringe sold by Abbott Laboratories is used both for hypodermic injections directly through the patient's skin and also for injections through a standard reseal on a patient venous access device such as a catheter for example.

The Abboject emergency syringe system includes a calibrated glass vial prefilled with a medical solution and a matching vial injector. The vial injector (or syringe housing) includes an integral delivery needle that can be used to inject the medical solution directly into a patient or into a reseal on an access device such as an I.V. tubing administration set or an I.V. container connected to a patient. The standard Abboject syringe is manufactured with the delivery needle enclosed by a removable needle hood to protect against accidental needle stick. The hood also protects the sterile needle from contamination prior to use.

Today, both patients and healthcare providers are constantly at risk of accidental needle stick from exposed needles. Needles used for hypodermic injections pose a risk of infection from blood borne diseases such as AIDS and hepatitis. Currently there are many efforts to reduce the number of exposed needles in the healthcare environment, especially in emergency situations. These efforts include minimizing the need for direct hypodermic injections into a patient by providing I.V. administration sets with reusable and/or multiple access sites. Additionally, removable and permanent needle guards such as the Lifeshield Abboject emergency syringe with needle guard are provided when sharp needle syringes are needed. Recently, blunt cannula and prepierced reseals are increasingly used for I.V. connections rather than traditional sharp needles and pierceable reseals. Alternatively, luer fitment connections are increasingly used in I.V. set connections in place of sharp needles and reseals.

Emergency syringes that are used for drug administration at injection sites on I.V. tubing sets also expose the healthcare provider to an additional type of accidental needle stick. Besides a life-threatening blood infection that may have infiltrated from the patient's blood system to the needle, the provider may be exposed to the side effects of drug residue in the needle.

Therefore it is desirable to provide an emergency syringe system that decreases the risk of accidental needle stick yet is readily capable of various configurations for the different connection procedures currently used, such as needle or luer connections.

Furthermore, it is also desirable that the safety and configuration features can be added to the standard Abboject syringes currently manufactured for hypodermic injections, and also to the Lifeshield Abboject syringe with guarded needle for I.V. set connections, thus providing continuity, economy and flexibility in product manufacture.

An example of a protective sheath and cap for a syringe needle is shown in U.S. Pat. No. 4,232,669 to Nitshke. The syringe is intended for use with an additive port of a flexible bag and therefore the sheath does not extend beyond the needle point. The sheath and a removable protective cap maintains the sterility of the syringe needle. However, the health care provider is at risk of accidental needle stick when the protective cap is removed. The sheath of Nitshke is attached to the syringe by an collar engaging the needle hub and therefore a sheath similar to the one suggested by the Nitshke disclosure could not be added to the standard Abboject syringe without extensively redesigning the Abboject syringe and the Abboject syringe manufacturing process. The current Abboject needle hub is already used as a friction fit for the needle hood.

A protected needle is also disclosed in U.S. Pat. No. 4,834,716 to Ogle. In FIG. 2 of Ogle, the protective sheath is fixed to the needle hub of the syringe. As previously discussed, fixing a protective sheath to the needle hub as suggested by Ogle does not allow a needle hood to be attached to the hub of the standard Abboject syringe as currently manufactured.

It is desirable to provide an emergency syringe for dual use with either a needle and reseal connection or alternatively a luer connection.

It is desirable that the luer connection and the needle connection components already be assembled to the emergency syringe so that the syringe is ready to use without having to add components during the emergency procedure.

It is desirable that the emergency health care provider can make either a luer connection or can make a needle to reseal connection by only having to remove a selected cover element.

It is therefore a primary object of the present invention to provide a luer adapter assembly for the Abboject emergency syringe so as to facilitate easy use in an emergency situation and to protect the healthcare provider from accidental needle stick.

It is another object of the present invention to add a luer adapter assembly to currently manufactured Abboject and Lifeshield Abboject syringes so that the syringes may be more safely and flexibly used with various I.V. set access devices.

It is another object of the present invention to protect the sterilized needle and luer adapter fitment connection from contamination until either is used.

It is another object of the present invention to provide easy and safe conversion of an emergency syringe from a needle and reseal connection to a luer connection.

SUMMARY OF THE INVENTION

The present invention is directed to a prefilled emergency syringe that includes a removable luer adapter assembly.

The preferred embodiment of the invention includes a removable luer adapter assembly that can be used in conjunction with a protective sheath mounted to the front wall of the syringe housing and coaxially extending with the delivery needle. An annular clearance space is maintained between the needle hub and the interior of the cylindrical sheath for the luer adapter assembly to be frictionally fit on the hub, preferably after the sheath is attached.

More particularly the adapter assembly includes a hollow, cylindrical tube which fits over and extends beyond the sharp end of the syringe needle. A tapered fitment at the proximal end of the tubular adapter is attachable to the tapered needle hub. The tubular adapter also includes a luer fitment at the distal end of the tube and a locking mechanism, such as a threaded lock, surrounding the distal luer fitment. A removable cap is attachable over the luer fitment and secured to the locking mechanism to initially close the tube. A force applied to the cap in one direction removes the cap from the locking mechanism. A force applied to the cap in the opposite direction removes the whole tubular adapter assembly from the tapered hub.

Other advantages and features of the present invention will become apparent from the following detailed description, the accompanying drawings and the appended claims.

BRIEF DESCRIPTION OF THE DRAWINGS

FIG. 1 is a cross section of the preferred embodiment of the present invention showing an emergency syringe injector housing, an attached hollow protective sheath, and a removable luer adapter assembly;

FIG. 2 is an exploded cross section of FIG. 1 showing the hollow sheath and luer adapter assembly prior to attachment to the syringe housing;

DETAILED DESCRIPTION OF THE PREFERRED EMBODIMENT

Figure 3:
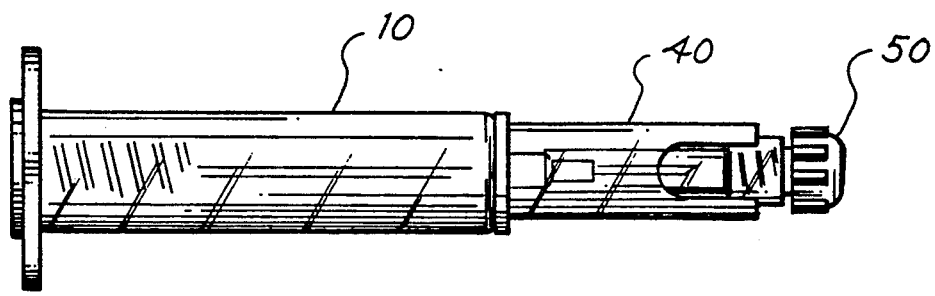
FIG. 3 is a side view of an assembled syringe injector system according to the present invention prior to use.

FIGS. 1 and 2 show a cross section of a preferred embodiment of the present invention including a syringe injector housing 10 and a hollow protective sheath 12 attached at the forward end 14 of the injector housing. The syringe injector housing 10 is an elongated hollow cylinder typically constructed of a molded plastic. The injector housing is open at the rear end 16. A removable cap 18 closes the rear end of the housing until the prefilled glass vial (not shown) is attached.

Front wall portion 20 substantially closes the front end of the syringe injector housing. An integrally molded needle hub 22 extends forward from the front wall and secures a needle cannula 24 within the syringe housing. The cannula 24 extends forward from the hub 22 to a sharp front delivery point 26 and rearward to a sharp rear point 28 near the distal end of the injector housing.

A glass vial (not shown) is prefilled with a solution, sealed with a slidable stopper, and sterilized. The vial and stopper are engaged with the rear end 16 of the syringe injector housing such that the slidable vial stopper is pierced by the rear needle point 28 so as to provide fluid communication with the needle cannula 24.

As previously described in co-pending U.S. patent application Ser. No. 07/765,356 filed Sept. 25, 1991, now abandoned and titled Needle Guard Assembly for Syringe, the disclosure of which is hereby incorporated by reference in this application, the hollow protective sheath 12 is attached to the front wall portion 20 of the syringe housing coaxially with the delivery needle 24. The hollow protective sheath 12 can be a separately molded hollow cylinder having an interior clearance diameter sized to accommodate the diameter of a reseal inserted in the sheath to engage the needle. The sheath is also sized to accommodate the luer adapter assembly 40 which will presently be described. Alternatively the sheath can be integrally molded with the injector housing 10.

The forward open end of the sheath extends longitudinally forward beyond the front needle point 26 of the cannula. The open end at the rear of the separately molded hollow sheath 12 has a flange 30 that is constructed to circumferentially abut the front wall portion 20 of the syringe housing. The sheath 12 can be mounted on the syringe housing 10 by various joining techniques such as spin welding, solvent bonding or ultrasonic welding, or it can be integrally molded with the housing.

The sheath 12 is positioned on the front wall 20 of the syringe housing with a radial clearance between the hub 22 and the interior of the sheath. The removable luer adapter assembly 40 includes a tubular adapter extension 42 having an internal taper 44 at the proximal end. A male luer fitment 46 is integrally formed at the distal end of the tubular extension. The luer fitment is circumferentially surrounded by a locking mechanism such as a threaded lock extension 48. The assembly 40 also includes a removable cover such as threaded cap 50 attachable to the threaded locking mechanism. The luer adapter assembly 40 is sized to occupy the annular clearance space that is maintained between the needle hub 22 and the interior of the sheath 12. The clearance space allows the whole luer adapter assembly 40 to optionally be attached to the hub 22 after the sheath 12 is attached to the injector housing. Also the axially unobstructed clearance space allows the luer adapter assembly 40 to be readily removed from the hub of the injector housing 10 to expose the delivery needle 24 within the sheath 12.

Each of the alternatively assembled embodiments described above requires a clearance between the needle hub 22 and the interior of the cylindrical sheath 12 for the luer adapter assembly 40. In the current manufacturing process for a standard Abboject emergency syringe, a removable needle hood (not shown) is attached by a friction fit to the needle hub 22. For Lifeshield Abboject syringes intended for dual use as either an I.V. needle connector or a luer fitment connector, the needle hood is removed and replaced by the luer extension assembly 40. The tubular luer adapter extension 42 and cap 50 functions as a needle hood for the needle or luer fitment prior to use. Thus substantially all standard Abboject syringes, whether for use as a standard hypodermic syringe, or modified as a Lifeshield Abboject syringe with a guarded needle for use at an I.V. tubing set reseal, or assembled with a luer adapter assembly according to the present invention can be assembled from standard Abboject syringes initially produced on the existing Abboject production line.

The luer adapter assembly 40 permits the Abboject syringe of the present invention to be packaged in a conventional package and sterilized in a conventional manner, such as by ETO sterilization or radiation sterilization. The interior of the sheath 12 does not need to be maintained sterile. Therefore a closure is not needed to cover the open end of the sheath. Furthermore, since the sheath interior does not need to be maintained sterile, the connection between the base of the sheath 12 and the front wall 20 of the injector housing does not need to be sealed. The connection only needs to provide a strong and solid anchor for the sheath 12 to the face of the housing.

In the preferred embodiment of the present invention, the connection is solidly supported by and anchored to the wall 20 of the housing. This is in distinction to alternatively known safety and adapter assemblies that are supported on the smaller diameter needle hub. The sheath construction of the present invention provides stronger protection for the hub and needle.

When initially installed, as best seen in FIG. 3, the luer adapter assembly 40 covers and protects the needle 24 while the sheath 12 protects both the needle and the luer adapter assembly. The luer adapter and cap assembly also provides a sterilizable enclosure for the needle 24 and the luer fitment 46 and helps maintain the sterility of both until used.

The sheath 12 includes at least one cutout 54 at the open front end of the sheath. The depth of the cutout accommodates different configurations of reseal injection sites such as Y-sites usable with the needle connection.

The tubular adapter extension 42 includes a male luer fitment 46 circumferentially surrounded by a locking mechanism 48 such as an axial flange having internal locking threads. The removable cap 50 also has mating threads 52. The cap can be removed from the locking threads 48 by twisting the cap in the opposite direction of the threads so as to unthread the cap. By twisting the cap in the same direction of the threads (i.e. in the 'on' or 'tighten' direction), the whole luer adapter assembly 40 can be removed from the needle hub 22.

Figure 4:
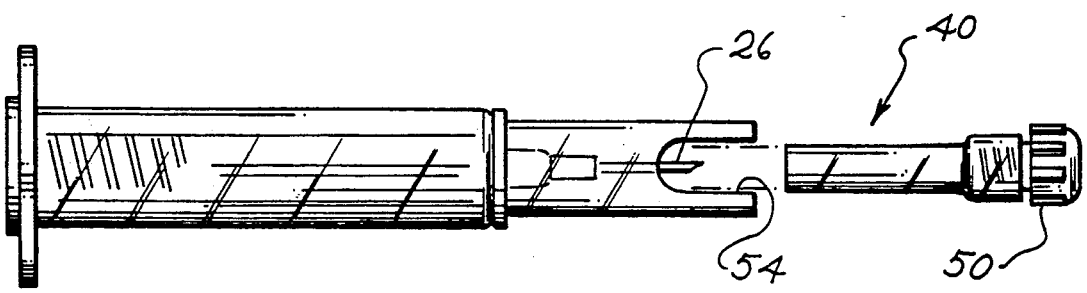
FIG. 4 is a partial cross section of the syringe injector system according to the present invention that is configured for use with a reseal connector.
Figure 5:
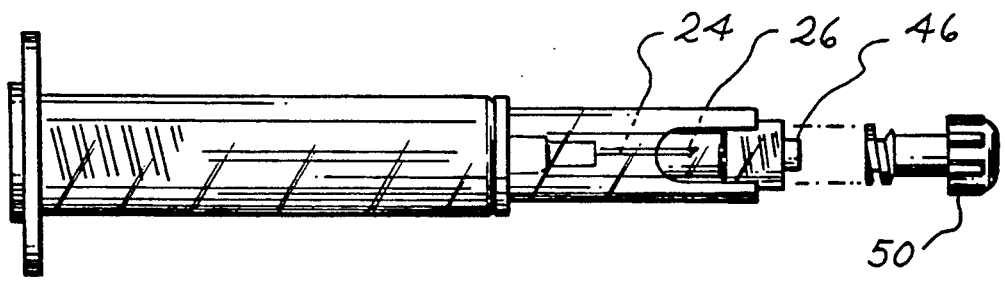
FIG. 5 is a partial cross section of the syringe injector system according to the present invention that is configured for use with a standard luer fitment connector.

It will be apparent from the foregoing description that the luer adapter assembly of the present invention not only protects the healthcare provider from inadvertent or accidental needle sticks, but also provides additional advantages. The removable luer adapter assembly 40 maintains the sterility of the needle 24 and luer fitment 46 after sterilization until the needle or luer connection is used. With only the adapter cap 50 removed and the luer adapter extension 42 still in place, as best seen in FIG. 5, the syringe can be used to make a luer connection. With the whole luer adapter assembly 40 removed, as best seen in FIG. 4, the needle 24 of the syringe injector can be connected to a standard reseal.

Although the present invention has been disclosed in terms of a preferred embodiment, it will be apparent to those skilled in the art that variations and modifications can be made without departing from the spirit and scope of the invention as defined in the following claims.

I claim:

1. A syringe having a cylindrical, closed-end injector housing portion, a tapered hub circumferentially extending from the closed end of the injector housing portion, a cannula extending from the tapered hub, and a removable luer adapter assembly positioned over the cannula, the adapter assembly comprising:

an axially extending hollow tube having a proximal end, a distal end, and a length greater than the extending cannula;

an interior taper at the proximal end of the hollow tube for attachment to the tapered hub;

a luer fitment with locking means at the distal end of the hollow tube; and a removable cap attachable to the locking means for closing and covering the luer fitment at the distal end of the hollow tube so that a force applied to the cap in a first direction removes the cap from the locking means and a force applied to the cap in a second direction removes the hollow tube and attached cap from the tapered hub.

2. The syringe of claim 1 further including a hollow sheath having a first and second open end, the first open end circumferentially attached to the closed end of the injector housing portion so that the luer adapter assembly fits within the inner diameter of the sheath and extends beyond the second open end of the sheath.

3. The syringe of claim 1 wherein the locking means is a threaded lock extension circumferentially surrounding the luer fitment.

4. The syringe of claim 3 wherein the force applied in the first direction is in the opposite direction of the threads of the threaded lock and the force applied in the second direction is in the same direction as the threads of the threaded lock.

5. The adapter assembly of claim 1 further including a friction fit between the interior taper at the proximal end of the removable tube and the tapered hub so as to provide a sterile and fluid tight enclosure around the extending cannula.

6. The luer adapter assembly of claim 2 wherein the first open end of the sheath has two oppositely disposed cutouts.

* * * * *